US011766180B1

(12) United States Patent
Newton (10) Patent No.: US 11,766,180 B1
(45) Date of Patent: Sep. 26, 2023

(54) IDENTIFICATION OF A TRUE FEBRILE STATE IN HUMANS THROUGH COMPARISON OF SIMULTANEOUSLY MEASURED CORE AND PERIPHERAL TEMPERATURES

(71) Applicant: Mark Newton, Wilmington, DE (US)

(72) Inventor: Mark Newton, Wilmington, DE (US)

(*) Notice: Subject to any disclaimer, the term of this patent is extended or adjusted under 35 U.S.C. 154(b) by 280 days.

(21) Appl. No.: 17/247,327

(22) Filed: Dec. 7, 2020

(51) Int. Cl.
*A61B 5/01* (2006.01)
*A61B 5/00* (2006.01)
*G16H 50/30* (2018.01)

(52) U.S. Cl.
CPC ............ *A61B 5/01* (2013.01); *A61B 5/746* (2013.01); *G16H 50/30* (2018.01); *A61B 2560/0252* (2013.01); *A61B 2562/0271* (2013.01)

(58) Field of Classification Search
CPC ... A61B 5/01; A61B 5/746; A61B 2560/0252; A61B 2562/0271; G16H 50/30
See application file for complete search history.

(56) References Cited

U.S. PATENT DOCUMENTS

| | | |
|---|---|---|
| 4,232,684 A | 11/1980 | Chervitz |
| 4,333,477 A | 6/1982 | Chervitz |
| 4,509,533 A | 4/1985 | Chervitz |
| 5,829,878 A | 11/1998 | Weiss et al. |
| 5,844,862 A | 12/1998 | Cocatre-Zilgien |
| 5,923,258 A | 7/1999 | Tseng |
| 6,447,474 B1 | 9/2002 | Balding |
| 6,851,850 B1 | 2/2005 | Lee |
| 6,852,085 B2 * | 2/2005 | Rubinstein ............. G16H 40/67 600/549 |

(Continued)

FOREIGN PATENT DOCUMENTS

| | | | |
|---|---|---|---|
| EP | 2459976 B1 * | 11/2018 | ............... G01K 1/16 |
| WO | 2004/110248 A2 | 12/2004 | |

OTHER PUBLICATIONS

International Search Report and Written Opinion of the International Searching Authority dated Feb. 4, 2022, issued in corresponding International Application No. PCT/US2021/060827, filed Nov. 24, 2021, 8 pages.

*Primary Examiner* — Christopher Koharski
*Assistant Examiner* — Gabriel Victor Popescu
(74) *Attorney, Agent, or Firm* — Patrick J. Stanzione; Stanzione & Associates, PLLC (57) ABSTRACT

Disclosed is the measurement, identification, knowledge inference and notification alerting of fevers within individuals. Embodiments according to the present disclosure include a system for measuring at least two body temperatures. The first temperature is measured from a body region that correlates with deep body temperature; the second is measured from body regions capable of subcutaneous/deep tissue vasoconstriction. Temperatures of the first region are automatically compared to cutoff thresholds, and differences between the first and second regions are automatically compared to temperature difference thresholds. This apparatus automatically evaluates if none, one, or both thresholds have been exceeded. If none or one, then a subject can be identified as normal (afebrile). If both thresholds are exceeded a screening or test subject identified as febrile, where actions can be taken to isolate individuals to prevent spreading of communicable diseases.

21 Claims, 6 Drawing Sheets

(56) References Cited

U.S. PATENT DOCUMENTS

| | | |
|---|---|---|
| 7,004,910 B2 | 2/2006 | Lindsey |
| 7,340,293 B2 | 3/2008 | McQuilkin |
| 7,548,776 B2 * | 6/2009 | Sheu .................. A61B 5/015 600/474 |
| 7,854,550 B2 | 12/2010 | Chan et al. |
| 8,593,251 B2 | 11/2013 | Heller |
| 8,663,106 B2 | 3/2014 | Stivoric et al. |
| 9,470,584 B2 * | 10/2016 | Pompei ................ A61B 5/01 |
| 9,521,335 B2 | 12/2016 | Mestha et al. |
| 9,618,401 B2 | 4/2017 | Heller |
| 9,927,305 B2 | 3/2018 | Pompei et al. |
| 9,974,441 B2 | 5/2018 | Lartey et al. |
| 10,548,763 B2 | 2/2020 | Paradis et al. |
| 10,568,760 B2 | 2/2020 | Paradis |
| 10,726,956 B2 | 7/2020 | Jiang et al. |
| 10,750,953 B1 | 8/2020 | Chase |
| 2003/0167034 A1 | 9/2003 | Balding |
| 2004/0254472 A1 | 12/2004 | McQuilkin |
| 2006/0178582 A1 | 8/2006 | Sheu |
| 2007/0071066 A1 | 3/2007 | Weng et al. |
| 2007/0153871 A1 | 7/2007 | Fraden |
| 2008/0154138 A1 | 6/2008 | McQuilkin |
| 2009/0175317 A1 | 7/2009 | Chan et al. |
| 2010/0042013 A1 * | 2/2010 | Cuesta Frau ............ A61B 5/01 600/549 |
| 2010/0152606 A1 | 6/2010 | Menashe |
| 2014/0149065 A1 | 5/2014 | Pompei et al. |
| 2014/0207405 A1 | 7/2014 | Heller |
| 2015/0316419 A1 | 11/2015 | Punnakkal |
| 2016/0302671 A1 | 10/2016 | Shariff et al. |
| 2016/0367149 A1 | 12/2016 | Lartey et al. |
| 2017/0156594 A1 * | 1/2017 | Sitvoric ................ A61B 5/01 |
| 2017/0049333 A1 | 2/2017 | Heller |
| 2017/0095158 A1 * | 4/2017 | Husheer ................ A61B 5/01 |
| 2017/0128052 A1 * | 5/2017 | Han ........................ A61B 5/01 |
| 2017/0354534 A1 | 12/2017 | Paradis et al. |
| 2018/0046778 A1 | 2/2018 | Jiang et al. |
| 2018/0085070 A1 * | 3/2018 | Chen ...................... A61B 5/01 |
| 2018/0242850 A1 | 8/2018 | Ellis et al. |
| 2019/0125011 A1 | 5/2019 | Eisenbrey et al. |
| 2019/0374387 A1 | 12/2019 | Ribble et al. |
| 2020/0060553 A1 * | 2/2020 | Tsuchimoto ............ A61B 5/01 |
| 2020/0146557 A1 | 5/2020 | Cheung et al. |
| 2020/0194115 A1 | 6/2020 | Chou |
| 2020/0214649 A1 * | 6/2020 | Cogely .................. A61B 5/746 |
| 2020/0253483 A1 | 8/2020 | Chase |
| 2020/0268549 A1 | 8/2020 | Paradis et al. |
| 2020/0288983 A1 | 9/2020 | Telfort |

* cited by examiner

IDENTIFICATION OF A TRUE FEBRILE STATE IN HUMANS THROUGH COMPARISON OF SIMULTANEOUSLY MEASURED CORE AND PERIPHERAL TEMPERATURES

TECHNICAL FIELD

The present disclosure is directed generally to detecting, measuring, or recording infections in humans for diagnostic purposes.

SUMMARY OF DISCLOSURE AND BACKGROUND INFORMATION

It has long been understood that pathogenic infection frequently results in a pathophysiological fever response. Fever, while a commonly used term to describe many diseases and physiological conditions, lacks a formally accepted definition. For the purposes of this disclosure, "fever" refers to abnormal body temperatures. In this context, fever is often described as a complex physiologic response to disease, mediated by pyrogenic cytokines and characterized by a rise in deep body temperature, generation of acute phase reactants, and activation of immune systems.

Body temperature characterizations of crowds in public spaces may be undertaken using non-contact infrared temperature transducing systems. While these systems identify elevated skin temperatures, which in turn infer elevated body temperatures, they are unable to differentiate between elevations caused by environmental and athletic stresses and those related to fevers caused by infection.

Embodiments of the present disclosure offers advantages of quickly differentiating elevated body temperatures caused by environmental stresses, from those caused by febrile responses, thereby improving accuracies of fever screening tests and reducing incidences of false positives and negatives.

This subject matter relates generally to instantaneous fever measurement, identification, knowledge inference and alerting systems for individuals. Embodiments include capabilities for measuring at least two body temperatures. The first temperature is measured from a body region that correlates with deep body temperature; the second is measured from body regions capable of subcutaneous/deep tissue vasoconstriction. Temperatures of the first region are automatically compared to cutoff thresholds, and differences between the first and second regions are automatically compared to temperature difference thresholds. This disclosure evaluates if none, one, or both thresholds have been exceeded. If none or one, then a screened individual can be identified as normal (afebrile). If both thresholds are exceeded, a tested or screened individual is identified as likely febrile. Actions can be taken to quickly isolate febrile individuals to prevent spreading of communicable diseases.

DETAILED DESCRIPTION OF DISCLOSURE

Different methods may be used when predicting infection status. One method may measure individual body temperatures and compare these single point measurements to a set of standard values. An example of a fever definition published by the United States Center for Disease Control (US CDC), under several different codes, identifies a patient as febrile (having a fever), if he or she has a measured temperature of at least 100.4° F. (38° C.), or feels warm to the touch, or gives a history of feeling feverish. While convenient to describe fevers in this manner, body temperatures, without supporting physical and medical data are meaningless in characterizing febrile responses. Robustly defining thermal febrile responses may involve definitions for body temperature measurement sites, times of day, times after eating or drinking, specified characterizations of menstrual cycles (female), standard sets of environmental conditions and activity rates, and additionally, knowledge of individuals' age, health, acclimatization to heat and exercise, and quantifying differences due to seasonal variations, among other possible criteria.

Figure 1:
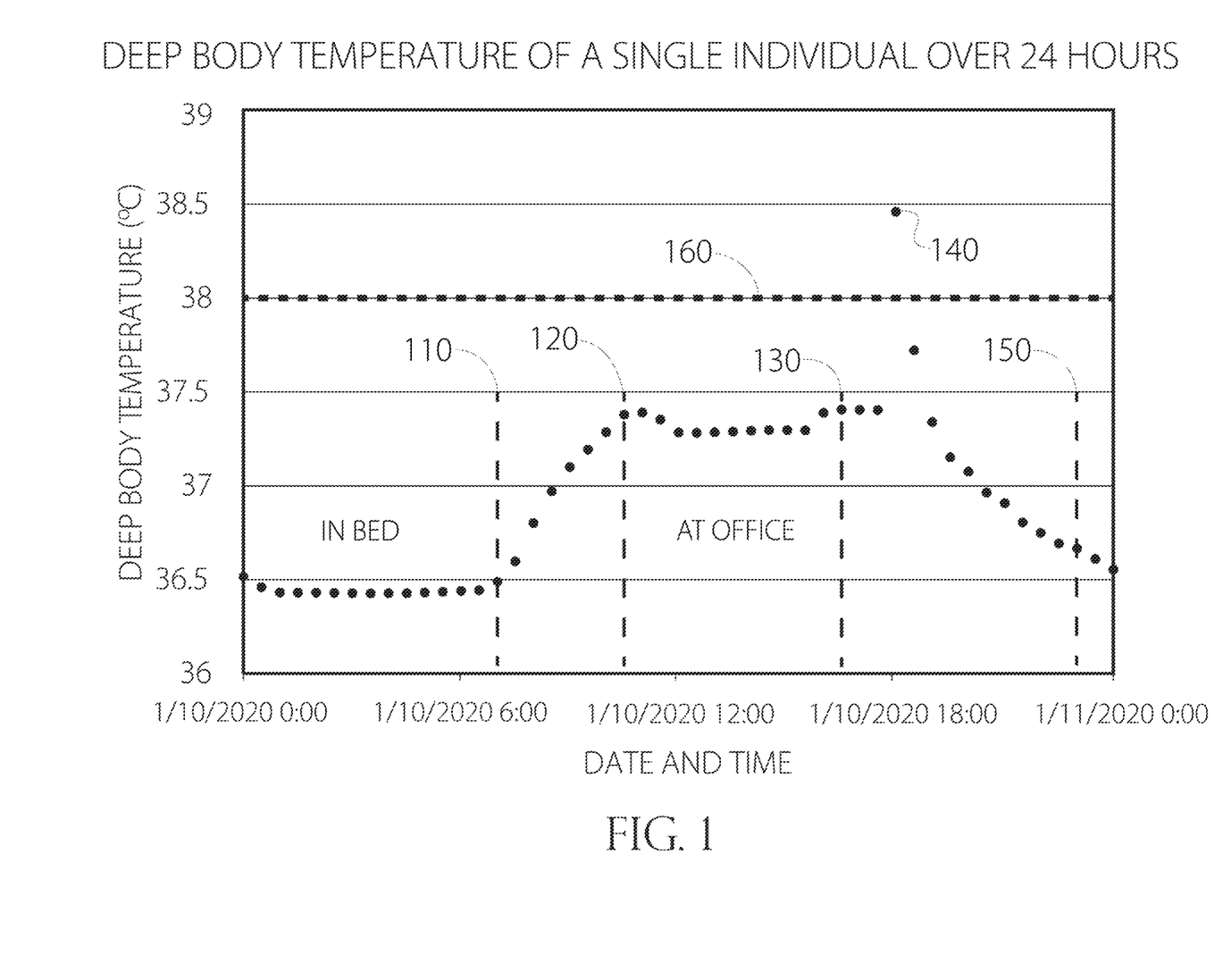
FIG. 1 shows an exemplary deep body temperature measured on an individual over a single day.

As a simplification, daily human temperature cycles are often represented using sine waves, the reality however, is that temperature cycles of individuals are significantly more complicated. Demonstrating the complexity of determining normal body temperature; FIG. 1 shows an example of a single normal (afebrile) individual's deep body (stomach) temperature captured over a 24-hour period, sampled at 30-minute intervals. The 'x' axis displays measurement time, while the Cy' axis displays body temperature. Measured temperature, represented by black circles, varies based upon time of day, environmental conditions, clothing, activity, and the like. While the subject is sleeping, to the left of 110, body temperature plateaus at a daily low value. When the subject rises and performs typical morning activities e.g. washing and eating in the region between 110-120, then body temperature starts to rise. As the daily routine varies, body temperature changes. In this example, the subject performs office work at a desk for most of the working day in the region between 120-130. After finishing work 130, the subject spends a period exercising, in which body temperature rises to a maximum of ~38.5° C. 140. In this non-limiting example, body temperature rise caused by exercise is ~1° C. In this example, the peak temperature of ~38.5° C. 140, continues to affect body temperature for hours after cessation of exercise activities. As the subject performs typical evening activities e.g. eating, socializing, resting, body temperature falls. After retiring to bed 150, subject body temperature falls back to a low plateau.

CDC febrile guidance temperature of 38° C. 160 is marked on FIG. 1 for reference. No two days for any individual are exactly the same, therefore, cyclical natures of circadian variations also change between days. Circadian variation tracks an individual's sleep wake cycle, which when synchronized with the day-night phase, is termed a diurnal cycle.

Normal body temperature is further complicated in females by menstrual cycle, where mean daily body temperature differences between mid-luteal and mid-follicular cycle phases may vary from 0.3 to 0.7° C.

Female monthly cycle temperature variation may be further complicated by contraceptive methods, pregnancy, and menopause. In a non-limiting example consisting of menopausal females, temperature variation is observed during "hot-flashes", caused by hormonal variations, which last between 15 and 120 minutes and may affect body temperature elevations of up to 1.5° C. several times daily.

Additional complications arise when distinct medical and commercial organizations measure temperatures in different body regions, using different procedures, devices and have their own standard threshold values for normal body temperature. Normal human body temperature may be described by the lowest plateau while resting, referred to as Basal Resting Temperature (BRT). As described above, body temperature is at its lowest during the low plateau, close to the middle of a normal sleeping period. Therefore, BRT is rarely measured in practice, but may be approximated by oral temperature sampled close to waking. BRT can be a particularly useful measurement basis for females attempting to become pregnant, as measuring oral temperature just after waking is a simple and repeatable method for individuals with no medical training.

Figure 2:
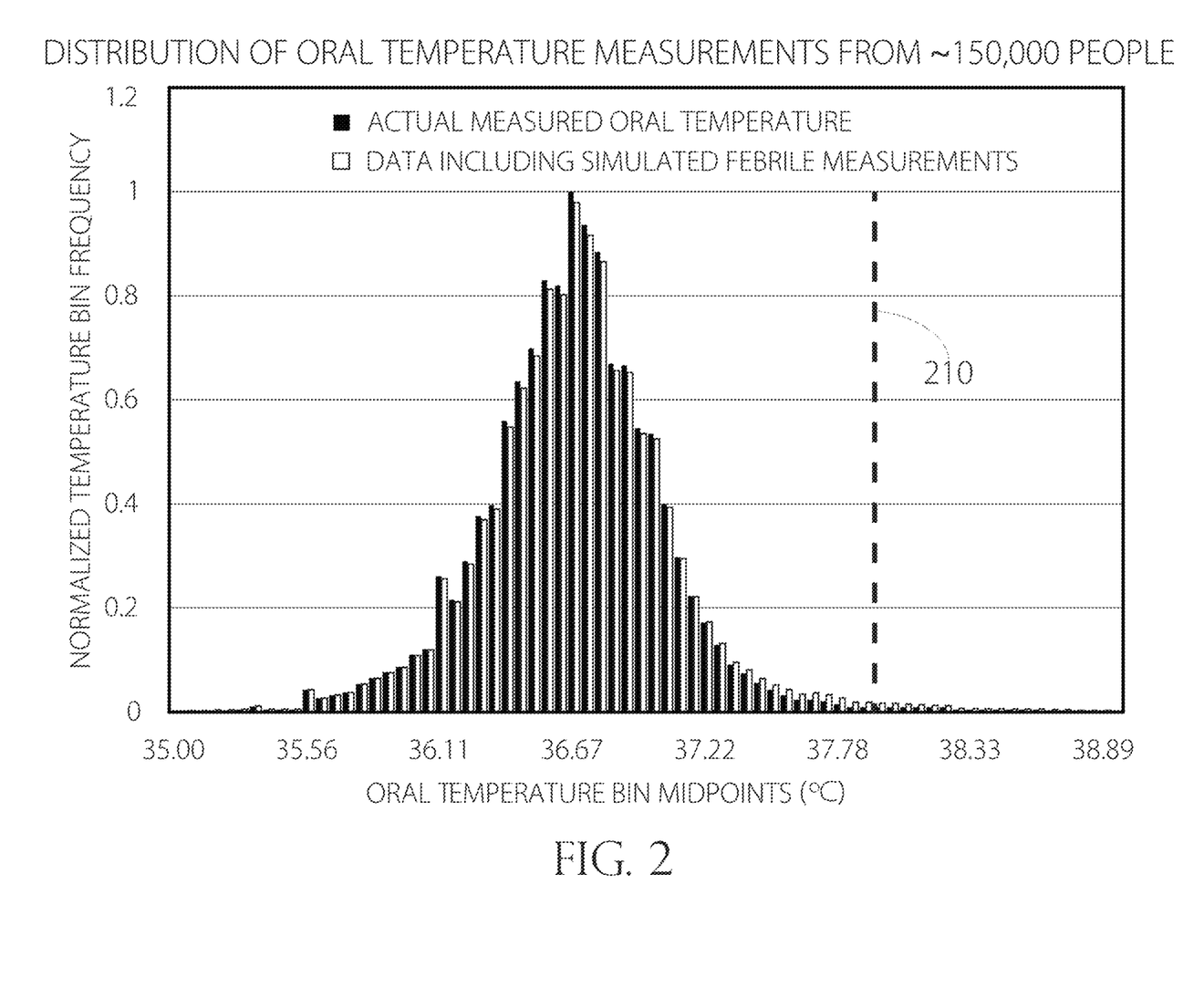
FIG. 2 shows a distribution of oral temperature measurements of many individuals, with an overlay of simulated data from febrile individuals.

FIG. 2 displays cohort data from the Stanford Translational Research Integrated Database (STRIDE), collected between 2007 to 2017. This data compiles over 570,000 oral temperature measurements collected from patient encounters of over 150,000 individuals during visits to Stanford Health Care. Oral temperatures were obtained by trained physicians, under controlled clinical conditions with digital thermometers, calibrated annually. Any observations having a diagnosis of fever at the time of examination were removed from the dataset. Statistics calculated from this dataset include an overall mean body temperature of ~36.7° C., the mean for males and females respectively is ~36.6° C. and ~36.8° C. (not shown), both have distributions of ~±1° C. Additionally, this data confirms correlations between oral temperatures and the time of day that the measurement was obtained.

A summary of the data is provided in FIG. 2, where oral temperature measurements are first grouped into 0.1° F. (0.0556° C.) bins, and the number of measurements in each bin are counted to determine the bin frequency. After counts are totaled, they are divided by the bin with the highest count i.e. the mode. This data is summarized in FIG. 2 as a normalized histogram distribution of oral temperature measurements. The x-axis shows midpoint temperatures of the 0.0556° C. (0.1° F.) bins and the y-axis displays normalized frequencies of each bin. Black bars in FIG. 2 illustrate normalized oral temperature measurements. The normalized data bin with the highest count, mode, has its midpoint at 36.6778° C. (98° F.). CDC febrile guidance temperature of 38° C. 210, is marked by the dashed vertical line for reference.

Infrared (IR) thermometers and thermal imagers may be employed in public and workplace spaces to identify individuals with elevated body temperatures in crowd situations. Infrared transducers detect emitted heat radiation, typically between wavelengths of 1-14 μm. These wavelengths have the advantage of being able to see temperatures. Thermographic cameras or thermal imagers are technologies employing arrays of infrared sensors that measure many emitted points of heat radiation over a field of view (FOV). Visualization software combines measurements from arrays to form an artificially colored image. Images from thermographic cameras use colors mapped to individual pixels to represent different temperatures, that is, different quantities of emitted radiation. Thermal imagers are particularly useful as they measure temperature at a distance i.e. non-contact and can map many temperatures in a single frame. As discussed above, normal body temperature varies throughout the day (and month), therefore, temperatures measured for the same individual early in the morning likely differ from those obtained in late afternoon. Additionally, environmental climates may significantly alter offsets between deep body and skin temperatures.

With supplementary software from artificial intelligence (AI) models, thermal imagers can automatically identify and isolate facial regions and provide average face, or partial face temperatures. Combined with software that adds cutoff temperature thresholds, these cameras may be used to identify individuals with facial skin temperatures above set values. Several limitations exist with infrared sensor arrays that should be accounted for in the accuracy of any predictions. Manufacturing methods used to produce these technologies are expensive and keep resolutions of thermal imagers far below their visible camera counterparts, often by 1-2 orders of magnitude. Observed resolutions from thermal imagers are highly dependent on objective distances, lens materials and quality, surfaces being measured e.g. color, dryness, texture, angle of incidence and the like, and ambient measurement environments. Additionally, offsets between skin and deep body temperatures do not remain constant and may vary greatly depending on environmental conditions.

Thermal imagers may be placed in high traffic access points of public spaces to provide alerts to trained operators when an individual with a specified body region exceeds a pre-defined constant value. This value may attempt to represent febrile individuals with deep body temperatures of >38° C. Thermal Imagers measuring skin temperatures can apply offsets to compensate for reductions caused by skin, fat, and bone, and thereby infer deep body temperatures. Due to the nature of these devices, selection of manufacturer and environment in which they are used, actual temperature cutoffs can be set at many different values, as can offsets for converting skin to deep body temperatures.

By making a few assumptions, it is possible to quantify the accuracies that these devices, or any other single point measurement of skin temperature, can provide. Clinical literature often defines febrile (in the thermal sense) as having an elevated body temperature that persists for an extended period. Febrile temperature elevations normally range between 0.5-2.0° C., though can exceed 3.0° C. in exceptional cases. A typical value used for fevers produced by common communicable diseases is an elevated temperature 1° C. above normal. Fevers can be acute or chronic, but for most flu, SARS, or Corona type viruses, they typically last between 1-7 days. For this example, an average fever length of 4 days is selected. If an assumption is made that during a disease outbreak, 10% of the population becomes infected during a specified month, with a mean fever length of 4 days, then using an idealized construct, 1.333% of the population is infected at any single measurement time.

If 1.333% of the population summarized in FIG. 2 is given a fever, raising their temperature by 1° C., then a composite population consisting of both febrile and afebrile individuals can be simulated. Results of this composite population are shown by the white bars on FIG. 2. Comparing the black to white bars, small changes are observed in the overall data distribution, shifting mean body temperature upwards.

TABLE 1

Statistical Results of 10,000 Single Point Temperature
Screening Test Groups on Composite Data from FIG. 2

| Temperature Cut-off (° C.) | True Negative TN | False Negative FN | False Positive FP | True Positive TP |
|---|---|---|---|---|
| 36.5 | 442 | 0 | 9425 | 133 |
| 37 | 3198 | 1 | 6669 | 132 |
| 37.5 | 8535 | 5 | 1332 | 128 |
| 38 | 9686 | 44 | 181 | 89 |
| 38.5 | 9804 | 116 | 63 | 17 |
| 39 | 9850 | 131 | 17 | 2 |

Table 1 displays statistical results of applying temperature cutoff thresholds to FIG. 2 composite data, where results have been scaled to represent 10,000 individual screening tests for each cutoff. As discussed above, for this nonlimiting example, 1.333% are febrile, resulting in 133 and 9867 febrile and afebrile individuals respectively during each testing cutoff. In this example, an offset of 0.5° C. has been added to composite data to convert oral to deep body temperatures. This offset value has been included for demonstration purposes only.

If cutoff thresholds are applied to everyone's measured temperature, then they either fall below that value, i.e. afebrile, or above the threshold, i.e. febrile. Column 1 of Table 1 displays six different upper threshold temperature cutoff values, where deep body temperature cutoffs have been evaluated with a 0.5° C. graduation, between 36.5-39° C. These results are split into four groups. Columns 2 and 5 display the correct test results for the composite population, where afebrile individuals are identified as afebrile (True Negative, TN) and febrile individuals are identified as febrile (True Positive, TP). Columns 3 and 4 display incorrect test results for the composite population, where febrile individuals are classified as afebrile (False Negative, FN) and afebrile individuals are classified as febrile (False Positive, FP). Each row of Table 1 sums to a total of 10,000 screening tests for all four groups.

While evaluating this type of epidemiological data, wrongly identifying afebrile individuals (False Positive Rate) are often considered less important than missing febrile individuals (False Negative Rate). However, additional complications arise during analysis of heavily biased populations, in this scenario 98.667% of the population should be identified as negative. Therefore, absolute numbers may be more important than portion of significance, resulting in type I errors (α) having different significance than type II errors (β), see below in Table 4. Reconciling the issues described above in rows of Table 1, interesting changes occur between 37.5-38° C. (oral+0.5° C.) temperatures. Between these two rows, the ratio of true positives to false negatives, changes from ~25:1 to ~2:1, and the false positive to true positive ratio changes from ~10:1 to ~2:1.

TABLE 2

Accuracy Calculations of Single Point Temperature
Tests on Composite Data from FIG. 2

| Temperature Cut-off (° C.) | Sensitivity TPR | Specificity TNR | Precision PPV |
|---|---|---|---|
| 37.5 | 96.2% | 86.5% | 8.8% |
| 37.6 | 92.5% | 91.8% | 13.1% |
| 37.7 | 88.0% | 94.9% | 18.9% |
| 37.8 | 83.5% | 96.5% | 24.1% |
| 37.9 | 75.9% | 97.6% | 29.8% |
| 38 | 66.9% | 98.2% | 33.0% |

Table 2 expands Table 1 rows between 37.5-38° C. to use 0.1° C. graduations between cutoff thresholds. Data displayed in Table 2 uses groups of individual screening tests for each cutoff, but further calculates statistics based on normalized group frequencies. Column 1 displays upper temperature cutoff thresholds in Celsius. Column 2 displays test Sensitivity or True Positive Rate (TPR) calculated by dividing the number of correctly identified febrile individuals by the total febrile population, i.e. TP/(TP+FN). Column 3 displays test Specificity or True Negative Rate (TNR) calculated by dividing the number of correctly identified afebrile individuals by the total afebrile population, i.e. TN/(TN+FP). Column 4 represents Precision or Positive Predictive Value (PPV), which calculates the number of correctly identified febrile individuals as a portion of the total number of positive test results i.e. TP/(TP+FP).

As illustrated in Table 2, the highest accuracy, as measured by precision is 33%, observed in the 38° C. row. At this temperature cutoff ~⅓ of the febrile population are misclassified as afebrile, and 7 out of 10 positive tests are false positives. Further, this is an idealized best-case estimate for any single point skin measurement test, as these results are calculated on high quality data captured by trained professionals under controlled clinical conditions, they include no variation associated with the measurement itself.

Under real use conditions, uncontrolled climatic environments and physical activities, temperature accuracies of thermal imagers verses calibrated digital thermometers, and offset differences of skin and deep body temperatures both within, and between individuals should be accounted for. It is estimated that when operated in real-use public environments, the highest expected precision of using any single point skin measurement test for fever identification, measured under uncontrolled conditions, is not more than 10%.

As demonstrated above, even with best case assumptions, a technical solution capable of quickly and easily identifying febrile individuals before they become a public hazard does not currently exist. The disclosure herein, describes an improved methodology and apparatus to accurately identify febrile individuals and provide data to be used to identify actions. This disclosure uses one-time measurements of at least two skin temperature sites, with threshold values that are not defined by traditional fever definitions.

Human thermoregulation is controlled between zones in which effectors act during different circumstances. Body temperature defense is primarily achieved through balancing metabolic heat production with convective, evaporative, and radiative heat losses to keep temperatures within thermal effector zones. Convective and radiative heat losses are modulated through skin temperature, which is in turn primarily regulated by vasodilatation/constriction responses. Evaporative heat loss can be additionally modulated through skin wetness, regulated by sweating. Additional factors such as shivering and non-thermal effectors e.g. loss of appetite, drive to reduce activity intensity and the like also contribute to thermal homeostatic balance.

Explanations of thermoregulatory responses in hot and cold environments date back over 120 years. Through combining traditional physiological knowledge, with better understanding, measurement technologies and logic processing can improve analyses of single time instance body temperature measurements.

Skin temperature variations of different body regions fluctuate depending on individual, age, sex, environmental factors, clothing, activity, fitness, medical conditions, and the like. Upper limits of skin temperature usually tend to ~1-2° C. below deep body temperature (when in air), though have been recorded higher in exceptional circumstances. Lower skin temperature limits for normothermic individuals vary greatly by region, with lowest temperatures normally experienced in peripheral body areas, that is hands, fingers, feet and toes. Thermal discomfort in these regions typically begins at temperatures>29° C. and most people feel pain if skin falls below 15° C. Under normothermic conditions, hand skin temperatures most often span 2-10° C. below deep body temperature. Exceptional cases exist where lower temperatures may be regularly observed in individuals with peripheral circulatory issues e.g. Peripheral Vasculature Disease (PVD) or Raynaud's disease, ~5% of the population. These disorders, most often observed in females, regularly cause premature peripheral occlusion and consequently, lower skin temperatures especially in hands and finger areas.

As described above, body heat loss regulation occurs through three main mechanisms, convection, evaporation, and radiation, all of which may be affected by environmental changes. Under normal conditions for humans in air, conduction of body heat usually accounts for <10% of total heat transfer. As environmental temperature, relative humidity (RH), air movement (including windspeed) and solar loads change, so does body heat balance and subsequently skin temperature. Skin temperature typically varies by an order of magnitude more than deep body temperature, and therefore environmental conditions have a much larger effect on skin. In a non-limiting example, under warm or hot conditions with high solar loads and minimal air movement, forehead temperature may be offset from deep body temperature by <1° C. Whereas a cold environment with moderate air movement, increased body heat transfer and/or cutaneous vasoconstriction (reduction in skin blood flow), may offset forehead temperature by 3-4° C. or more.

Examples of elevated body temperature occur during febrile responses. Febrile responses reset thermal effector zones to higher levels and may suppress sweating, reducing evaporative heat loss, initiate shivering, increasing metabolic energy production and occlude blood flow to skin and deeper tissues in peripheral body regions, thereby reducing peripheral skin temperatures and subsequent heat loss. Similar responses in shivering, sweating and peripheral blood flow may also occur when individuals are placed in cold environments or become hypothermic. Body regions in which deep tissue vasoconstriction may occur, reducing blood flow to skin, fat, muscle, and visceral tissues are typically located in the body periphery, and include lower legs, feet, lower arms, wrists and hands.

Another example of elevated body temperature occurs during hyperthermia. When activity and/or environmental factors cause a body to overheat, exceeding thermal effector zones, this is often referred to as hyperthermia. In these cases, physiological stimuli promote body temperature reductions by increasing heat loss. Increases in body heat loss may be achieved through higher sweat rates which promote evaporative mechanisms, and/or dilation of vessels to promote skin blood flow, thereby increasing skin temperature, which also improves conductive and radiative heat losses. During hyperthermia, body regions with high surface area to volume ratios e.g. hands and fingers, can be particularly efficient in removing excess heat.

Several improvements are disclosed that increase testing accuracy for infrared sensor devices. Non-limiting examples of these solutions for IR temperature systems and thermal imagers may include methods to measure different body regions with better temperature consistency e.g. wrists, eyes, neck, jaw and the like. Improvements in sensor array calibrations may also be achieved through including a black body reference within the FOV, providing a known temperature, enabling "on-the-fly" corrections of errors caused by atmospheric conditions or instruments. Additionally, use of multispectral bandpass filters can improve temperature estimates of surfaces with different emissivity values, as can training a specific device in a defined setting on a particular day.

While increasing instrument accuracies, none of these improvements aid in differentiating between elevated body temperatures caused by environmental factors from those caused by febrile responses.

Demonstrating this concept in a non-limiting example, two individuals are screened for skin temperature in a region closely tracking deep body temperature e.g. inner canthus of eyes, or parts of forehead. These individuals are screened using a system with a black body reference in the FOV, both are found to have the same temperature, and these exceed a predefined febrile temperature cutoff threshold. During further evaluations, the first individual is determined to be hyperthermic, and the second is determined to be febrile. If these further evaluations measure both individuals with respect to their thermal effector zones, then the hyperthermic patient will be attempting to remove heat, while the febrile patient will be trying to defend body temperature through reduced heat loss.

Figure 4:
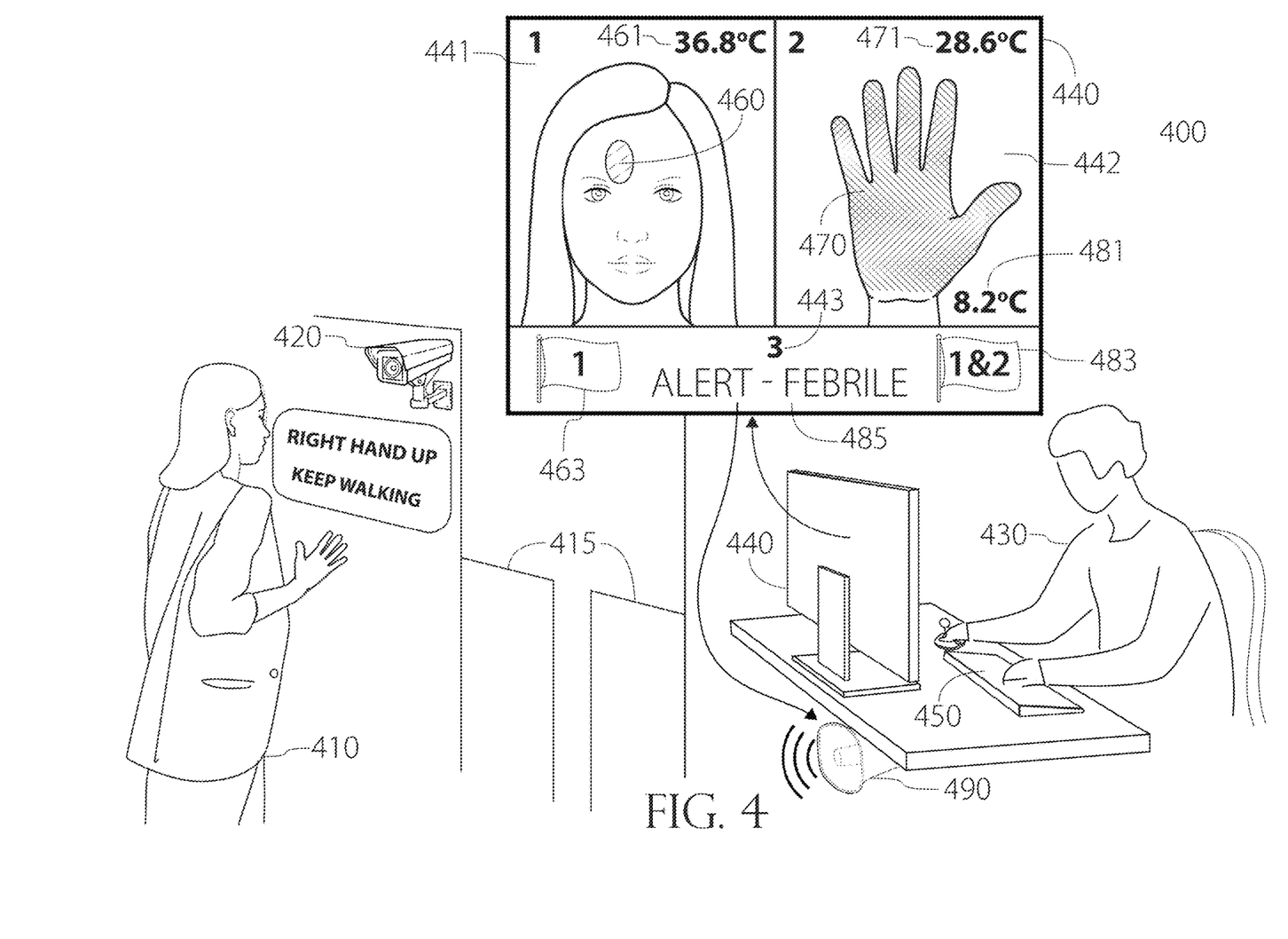
FIG. 4 shows a diagrammatic exemplary implementation of a febrile characterization and identification apparatus.
Figure 5:
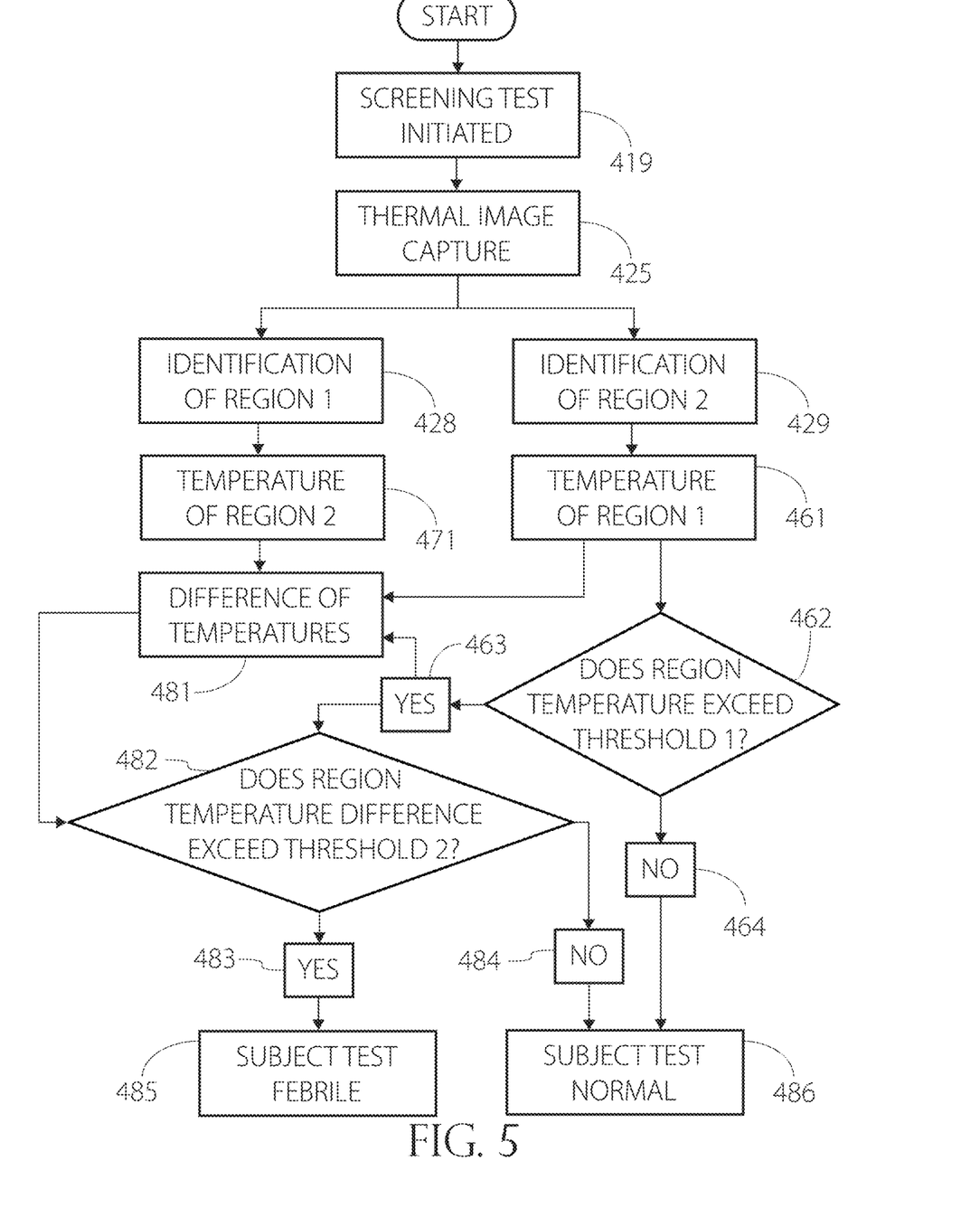
FIG. 5 is a block flow-diagram of the exemplary system development for the embodiment illustrated in FIG. 4.

One embodiment of this disclosure adds additional steps to the above example. Additional steps include measuring right hand palm temperatures, alongside temperatures of a small forehead region adjacent to the glabella and manipulating these to provide improved screening accuracies. This embodiment is illustrated in FIGS. 4 and 5 and discussed in detail below. Test results from this embodiment define partial forehead temperature as one region and palm and digit temperatures as a second region. While forehead temperature remains the same for both, palm and digit temperatures likely show differences between both test subjects. In attempting to remove excess heat, hypothermic individuals likely present with vasodilated palms, subsequently, these temperatures closely correlate with deep body (blood) temperature. Alternatively, febrile individuals may be likely attempting to minimize heat loss and have a tendency to have vasoconstricted palms, with hand skin temperatures well below deep body temperature.

For the remainder of this disclosure, a region that closely tracks deep body temperature is referred to as Region 1 and a region where significant reduction in blood flow may occur in deeper tissues is referred to as Region 2.

Solutions can measure skin temperatures of single points, or a single averaged body region to estimate deep body temperature. However, skin temperature offset differences from deep body, vary depending upon region selected, individuals and environmental conditions. If differences are calculated between Region 1 and Region 2, accuracy may be further improved by partially compensating for environmental and individual variation. In the first embodiment, an absolute elevated temperature threshold cutoff is applied to Region 1, and only if this cutoff is exceeded, is a maximum difference cutoff between Regions 1 and 2 evaluated to confirm febrile individuals attempting to minimize heat loss. This partial compensation occurs, as under typical conditions hand skin may vary significantly more than forehead skin temperatures.

Humans may experience competing mechanistic challenges, as described above, this may occur within individuals who suffer from vasculature disorders, e.g. Raynaud's disease. In typical cases of Raynaud's disease (primary or secondary), blood flow to extremities may be severely occluded, sometimes to the point of causing tissue whitening, significantly reducing skin temperature of these regions. If a patient suffers from vasculature disorder while concurrently being hyperthermic, then a constrictive drive from their disorder competes with a dilative drive to promote heat loss. Evidence from investigations studying these phenomena strongly suggest that under hyperthermic conditions, constrictive drives from PVD or Raynaud type disorders may be largely negated, and patients tend to function similarly to general populations.

Embodiments of this disclosure improve low precisions of single point skin temperature measurements through several methodologies. One of these uses confirmation testing of temperature differences between Regions 1 and 2 and applies maximum difference cutoff thresholds. In one embodiment, the temperatures of Regions 1 and 2 are measured concurrently and differences calculated for each test.

Figure 3A:
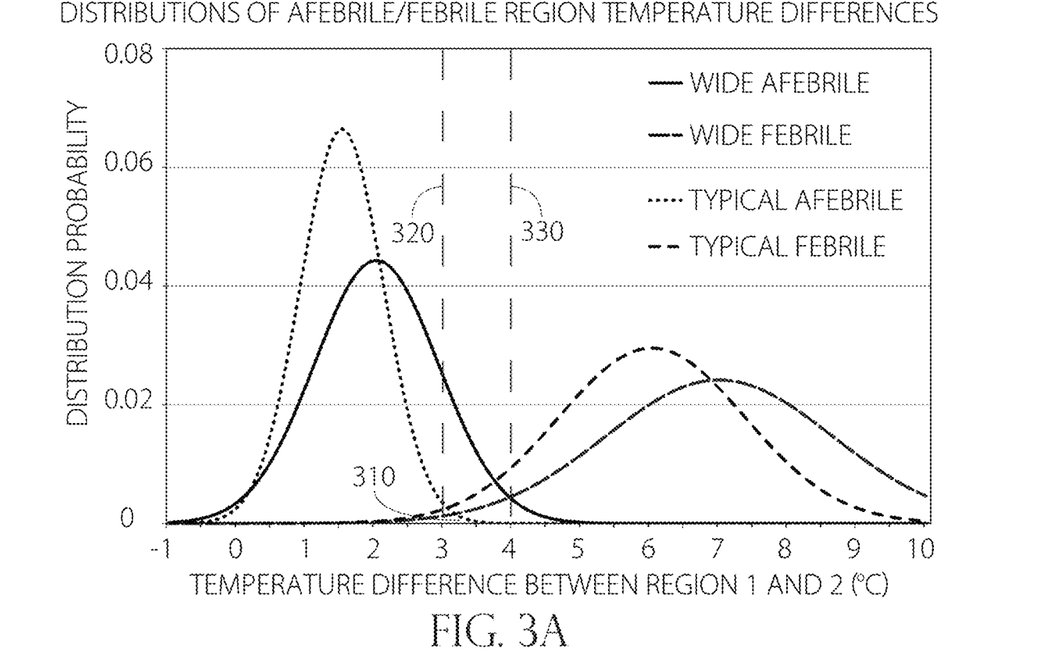
FIGS. 3A and 3B show exemplary graphical results of population temperature difference distributions.
Figure 3B:
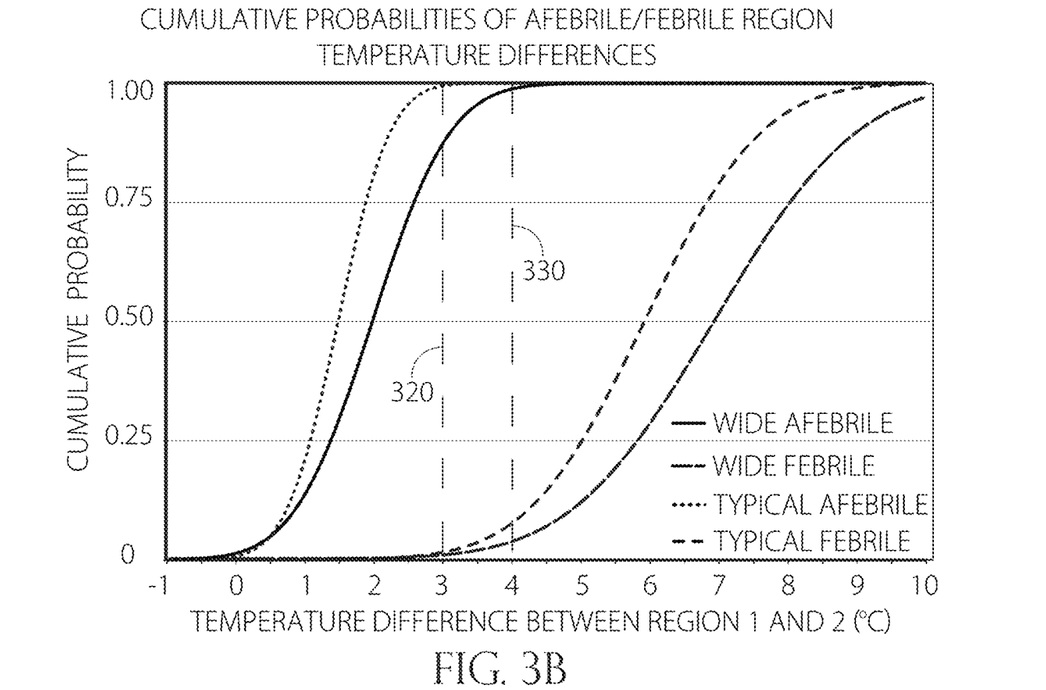

FIGS. 3A and 3B show exemplary graphical results of population temperature difference distributions. These examples represent idealized distributions of temperature differences between Regions 1 and 2 of febrile and afebrile populations. Exemplary results illustrated in FIGS. 3A and 3B are normally distributed. Two distributions are illustrated for each of the two populations, the first set of distributions, denoted as wide, represent distributions with highest expected observed deviation values for individuals of all ages, including previous medical conditions and variability due to data collection methodologies in both populations. Distributions labeled typical, represent expected results from typical populations. The x-axis shows temperature differences between Region 1 and Region 2. The y-axis of FIG. 3A shows distribution frequency probability using a Probability Density Function (PDF). The y-axis of FIG. 3B displays cumulative probabilities, calculated by a Cumulative Density Function (CDF).

Temperature differences for afebrile populations are estimated from a meta-analysis of human subject study data of hyperthermic subjects. Data for febrile populations may be difficult to obtain in this context, therefore, these distributions are approximated using a meta-analysis of afebrile subjects in normothermic states. Rationale for using this data to represent febrile populations, is to provide worst-case scenarios with the lowest precisions. If subjects were febrile, active vasoconstriction would likely be occurring in peripheral regions including hands, providing larger temperature differences between regions and even greater separation between febrile and afebrile distributions. Selected study criterion for both analyses used hand temperatures (Region 2) measured alongside at least one other skin temperature that closely correlates with deep body temperature. Studies were performed in thermoneutral or warm environments of >10° C. Where possible, forehead, face or head temperatures have been used as Region 1.

The data have been idealized for best fit to gaussian distributions and as such represent statistical constructs. The wide afebrile distribution has a mean ($\mu$) of 2° C. and a standard deviation ($\sigma$) of 0.9° C., while the typical distribution has $\mu$ and $\sigma$ values of 1.5 and 0.6° C., respectively. The wide febrile distribution has a $\mu$ and $\sigma$ of 7.1 and 1.65° C. respectively, while the typical febrile distribution has $\mu$ and $\sigma$ values of 6.1 and 1.35° C. respectively.

Data in FIG. 3A illustrates normalized population frequencies at temperature differences, between −1° C. i.e. Region 2 is 1° C. hotter than Region 1, to 10° C. i.e. Region 2 is 10° C. cooler than Region 1. Normalized frequencies ensure equal areas under each of the four distributions, i.e. unity area. The wide febrile data distribution ends at 12° C. difference (not shown). Quantifying test precisions at varying a and 13 values requires evaluating intersecting areas between febrile and afebrile distributions 310. For wide distributions, this intersecting region spans 2-5° C., and for typical distributions the intersection span is 2-3.5° C.

FIG. 3B data illustrates cumulative probabilities or total population portions with regional temperature differences below that of the respective x-axis temperature. Comparing FIG. 3A to FIG. 3B, accumulative probabilities of 1.0 occur at respective distribution end points in FIG. 3A. This data provides population portions for specific a and 13 values, that is, portions of misclassified afebrile and febrile individuals. The vertical lines 320 and 330 illustrate exemplary temperature difference cutoff thresholds where Region 2 is 3° C. and 4° C. cooler than Region 1.

Evaluating data for wide distributions for a temperature difference cutoff threshold of 3° C. 320, results in an 87.8% specificity and a 99.2% sensitivity. For FIGS. 3A and 3B, specificity is equivalent to the population portion to the left of line 320, that is for wide afebrile data 87.7% of afebrile individuals have a temperature difference of less than 3° C. between Regions 1 and 2. Similarly, sensitivity is equivalent to the population portion to the right of line 320, that is for wide febrile data 99.2% of febrile individuals have a difference of more than 3° C. between Regions 1 and 2. For a temperature difference cutoff threshold of 4° C. 330, 98.9% specificity and 96.3% sensitivity are observed.

The following analysis focuses solely on wide distributions, thereby providing worst case, lowest accuracy scenarios. Combining data from Tables 1 and 2 with this example, using cutoff temperatures for Region 1 of 37, 37.5 and 38° C., and cutoff differences between Regions 1 and 2 (from above) of 3° C. 320 and 4° C. 330, then overall screening test sensitivities and specificities can be calculated.

TABLE 3

Sensitivity and specificity of a combined temperature cutoff for Region 1(R1) and difference cutoff between Regions 1 & 2

| R1 Cutoff | 3° C. (R1-R2) | | 4° C. (R1-R2) | |
|---|---|---|---|---|
| (° C.) | Sensitivity | Specificity | Sensitivity | Specificity |
| 37 | 98.4% | 91.8% | 95.6% | 99.2% |
| 37.5 | 95.4% | 98.4% | 92.7% | 99.8% |
| 38 | 66.4% | 99.8% | 64.5% | 99.98% |

Table 3 presents exemplary accuracies of the proposed disclosure. Table 3 includes results from Tables 1 (37, 37.5 and 38° C. rows only) and 2, combined with additional temperature difference cutoff thresholds as described above. Combined screening sensitivities are calculated through multiplying the retained portion of the febrile population after Region 1 threshold has been applied, by the population portion retained after regional difference thresholds have been evaluated. Combined screening specificities are calculated by first multiplying the retained afebrile population portion after Region 1 threshold has been applied, with specificity after a difference threshold has been evaluated. To complete calculating screening specificity, this product is then added to the rejected afebrile population portion after evaluation of Region 1 threshold. Column 1 of Table 3 shows upper threshold cutoff temperature for Region 1. Columns 2 and 3 show combined sensitivities and specificities for regional temperature difference cutoffs of 3° C. and columns 4 and 5 for 4° C. These results are again based on a 1.333% febrile population.

TABLE 4

Alpha ($\alpha$), beta ($\beta$) and precision values from Table 3

| Combined Cut-offs (° C.) | Alpha $\alpha$ | Beta $\beta$ | Precision PPV |
| --- | --- | --- | --- |
| 37 & 3 | 8.2% | 1.6% | 13.9% |
| 37 & 4 | 0.8% | 4.4% | 68.2% |
| 37.5 & 3 | 10.5% | 4.6% | 44.2% |
| 37.5 & 4 | 0.2% | 7.3% | 89.1% |
| 38 & 3 | 0.2% | 33.6% | 80.4% |
| 38 & 4 | 0.02% | 35.5% | 97.7% |
| 37.3 & 3.9 | 0.4% | 5.2% | 75.4% |

Table 4 calculates $\alpha$, $\beta$ and precision values based upon Table 3 results. $\alpha$ may be calculated as 1—Specificity and represents the portions of afebrile individuals wrongly classified as febrile. $\beta$ may be calculated as 1—Sensitivity and represents portions of febrile individuals wrongly classified as afebrile. Precisions represent portions of correctly classified febrile individuals as percentages of total positive test results and are commonly used in combination with $\beta$ values and Receiver Operating Characteristic (ROC) curves (not shown) as bellwether indicators for evaluating medical tests.

Apparatus and methodologies of this disclosure predicted a reduction of false positives i.e. provide an improved a, and as expected this was observed. Examples illustrated in Table 2 show the highest precision at a Region 1 Cutoff of 38° C. and an $\alpha$ of 1.8%. Applying a difference cutoff of 4° C. alongside a region 1 cutoff of 38° C., further reduces a from a previous best of 1.8% to 0.02%, and precision is increased from 33% to 97.7%, that is, from 7 in 10 false positives to 2 in 100. However, using this new methodology, this may be far from the best result, as over ⅓ of febrile cases continue to be misclassified.

As discussed above, minimizing type II errors ($\beta$), in these types of situations may be often considered more important than minimizing type I errors ($\alpha$). Reducing screening test $\beta$ values requires temperature cutoff thresholds for Region 1 to be lowered. For examples illustrated in Tables 2 and 3, if screening tests were measured using partial forehead temperatures alone, then reducing temperature cutoff thresholds for Region 1 result in false positives, rendering the screening impractical. This is illustrated in 37.5° C. rows of Tables 1 and 2, where a low $\beta$ of 0.04 (1–0.962) provides a precision of 8.8%, which translates to more than 11 false positives for each true positive. Once again, this is an idealized scenario from a statistical construct, actual precision values may be even lower.

When using 2 or more temperature regions, high values of $\alpha$ and precision may be preserved at lower temperature cutoff thresholds for Region 1, where low $\beta$ values are also observed. This is counterintuitive for traditional single point measurement screening test methodologies, where cutoff thresholds are applied based upon febrile guidance temperatures. The lowest $\alpha$ and highest precision values in Table 4 are observed at a Region 1 cutoff temperature of 38° C. with a difference cutoff of 4° C. It may be that missing so many febrile individuals at these cutoffs provides unacceptable results and a threshold of 37-37.5° C. for Region 1 (oral temperature +0.5° C.), with a difference cutoff>4° C. may provide significantly better overall results. To expand this concept, focusing on acceptable compromises where both precisions and $\beta$ values may be enhanced, the last row of Table 4 illustrates a 37.3° C. Region 1 threshold and a 3.9° C. difference cutoff that results in both high precision and low 13 values. This non-limiting example provides a 13 value of 0.05 i.e. missing 5% of febrile individuals, an $\alpha$ of 0.004, and precision of 75.2%. Applying these results to the above example of 10,000 screening tests, affords 7 false negative and 39 false positive tests respectively, while reducing the false negative portion (precision) to 2.5 in 10.

This unexpected result makes embodiments of the disclosure more accurate. Using an oral+0.5° C. cutoff threshold of 37.3° C. in any single point measurement screening test may be impractical, yielding precisions close to 3.3% or 30 false positives for each true positive.

Therefore, the methodology of this disclosure achieves high precisions with acceptably low $\beta$'s, but only through development of rationales for setting Region 1 temperature cutoff thresholds which were not dependent on traditional definitions of thermal fevers. Instead, these new cutoff thresholds represent elevated body temperatures, where they may be set to values significantly below febrile guidance temperatures.

FIG. 4 illustrates a block diagram representation of an exemplary system 400 embodying the disclosure. In this embodiment, individuals 410 route through entry points 415, passing in front of a mounted thermal imager 420. Upon entering the facility, the individuals 410 raise their hand and are automatically scanned through intelligent software loaded on to the thermal imagers embedded processor board. Imagers are controlled and monitored by trained operators 430 through real-time display devices 440 and system controllers 450. In this embodiment, a Graphical User Interface (GUI) is presented on a display 440, the interface is split into three zones. Zone 1 441 displays a picture of this individual's Region 1 temperature, which for this embodiment covers partial forehead adjacent to the glabella illustrated by hatched region 460. Boundaries of Region 1 may be automatically identified using built in AI, where forehead colors (not shown) are mapped to temperatures between 20 and 45° C. Zone 2 442 displays a picture of Region 2. For this embodiment, Region 2 covers palm and digits of the right hand, highlighted by hatched region 470. As above, AI automatically identifies this region and maps colors to represent temperatures. Mean region temperatures 461 and 471 are displayed in the top right corners of zones 1 and 2, and temperature difference between regions 481 is displayed bottom right of zone 2. Zone 3 443 displays user results, including flags 463 and 483 and evaluated status 485.

This system provides automated responses of Region 1 average temperature and compares this to stored values for Region 1 cutoff temperature. If average Region 1 skin temperature exceeds the stored value, for this non-limiting example, a temperature cutoff of 36.1° C. then a flag 463 is displayed on the left side of zone 3. If Region 1 cutoff is exceeded, then the temperature difference between Regions 1 and 2 is calculated and displayed 481, and if this value exceeds a stored temperature difference cutoff threshold, in this embodiment 3.9° C., then a second flag 483 is placed on the right of zone 3. A febrile alert is automatically raised on the display 485 if both flags are present, and an audio warning may also be sounded 490.

Decision logic of the embodiment illustrated in FIG. 4, is further explained by the FIG. 5 block flow diagram representation. Upon an individual coming within range, a temperature screening test 400 is automatically started by triggering a Passive InfraRed (PIR) sensor 419, which may be located below the camera 420. The thermal imager first captures an image 425 of the individual and then isolates Regions 1 428 and 2 429, using AI software algorithms. After regions are identified, integrated mean temperatures of each region are calculated and may be displayed 461 and 471. Region 1 temperature is compared to a lookup table 462 and evaluated. If Region 1 temperature falls below the cutoff 464, the individual is identified as normal 485 and screening is complete. If Region 1 temperature exceeds the cutoff threshold, a flag 463 is shown on the left of zone 3 in this particular embodiment. Temperature difference is then calculated between Region 1 and 2, and may be displayed in zone 2 481. This difference is also compared to a lookup table 482. If the temperature difference is determined to be below a second threshold 484, then the individual is identified as normal 486 and screening is complete. However, if the individual is determined to have a temperature difference between regions above the difference threshold, a second flag is displayed 483 and the individual is identified as febrile 485. Upon being identified as febrile, the individual may be denied access to the facility until such time as they can be rescanned and pass the screening with a subject normal result, in one example.

Human bodies present many opportunities to measure skin temperatures. Areas available for screening tests using non-contact type measurements are typically restricted to naked skin regions within normal social settings, where devices cannot scan and measure clothed regions of individuals who pass within the FOV. Within those parameters, regions of unclothed skin are typically restricted to include face, mandible, neck and hands, e.g. facial regions are commonly used by thermal imagers to infer deep body temperatures.

Figure 6:
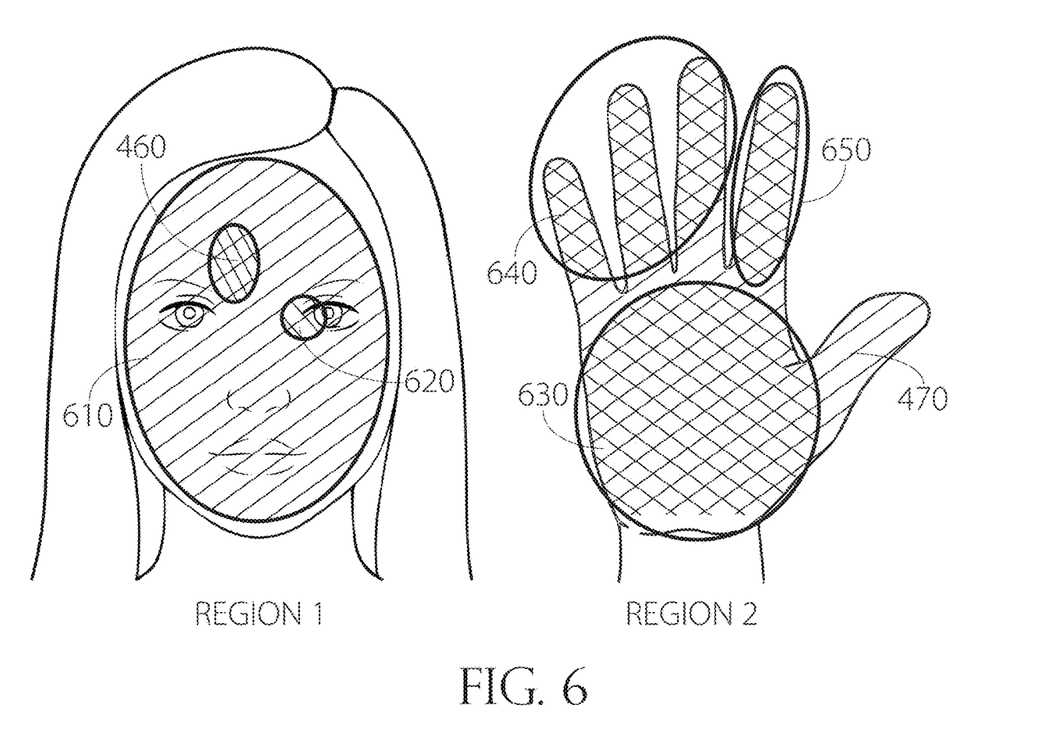
FIG. 6 shows a graphical representation of exemplary measurement areas for different body regions.

Within this context, FIG. 6 illustrates non-limiting site selections for Regions 1 and 2. Region 1 should select body areas that do not display deep tissue vasoconstriction due to thermal factors. For screening individuals in public environments, this renders site selection of facial regions 610 more preferable. FIG. 6, Region 610 covered by single and cross hatched areas may also be split into smaller areas, these may include full (not shown)/partial forehead 460 and smaller regions such as the inner canthus of the eyes 620. If any eye regions, especially around the inner canthi, are chosen for infrared types screening solutions, then eyeglasses and contact lenses should usually be removed as many eye glass lens materials are opaque to typical thermal imager wavelengths and temperatures behind lens materials are not easily measured. Neck regions (not shown) may also provide adequate inference of deep body temperature, particularly those around the facial branch of the carotid artery, though these are not always available in social environments due to coverings and facial hair.

Region 2 should select body regions that may vasoconstrict in typical thermal environments when a body becomes cold or under fever type stimuli. Temperatures at any of these sites may cause situations in which deep body temperature may be increasing, while the temperature of these regions may be simultaneously decreasing. In public environments, this renders site selection of hand and wrist regions 470 more preferable. FIG. 6, Region 470 covered by single and cross hatched areas may also be split into smaller regions, these may include palms 630, several different digits 640, single digits 650 or wrists (not shown).

In another embodiment three regions may be used. In such an embodiment, Region 1 may be the partial forehead adjacent to glabella 460, Region 2 may be the hand palm 630, and Region 3 may be the palmar index finger 650. In this embodiment, regions are identified using AI software that separates selected body areas from any background and calculates average regional temperatures. A cutoff is applied to the forehead and 2 temperature differences are evaluated between Regions 1 and 2, and Regions 2 and 3. Additionally, any regional temperature may also be a single point measurement that is not averaged over larger areas. In another embodiment, Region 1 is the cheek temperature and Region 2 is the index fingertip temperature, both measured by thermocouples in skin contact with these areas.

Physiological measurement hardware may include one or more of the functionalities listed below.

1. Contact/non-contact sensor modules capable of measuring temperatures between 0 and 50° C. Sensor module design and construction may be of analog, digital or smart module types. Sensor module specifications should include traceability for accuracy, calibration, and drift.
2. If not included within the sensor module itself, a separate signal amplification, signal conditioning and communication system may be used to interface with the input/output (I/O) interface of the device processor.
3. A power source capable of powering the device.
4. The device should contain a processor, memory, and an I/O interface capable of storing data until such time as it is successfully communicated or transmitted to additional platforms. The device may also contain volatile and other types of memory e.g. a Secure Digital (SD) memory card, though this is not a requirement.

Additionally, devices may measure using non-contact techniques, may average over skin regions or may measure several different regions simultaneously, though this is not a requirement.

Regional temperatures and regional difference evaluations may be made in single devices also containing the physiological measurement hardware, or in separate devices. Evaluation systems may include one or more of the functionalities listed below.

Systems:
1. may be capable of receiving regional temperature data from sensor modules I/O interfaces or from temperature measurement devices.
2. contain processing capability, either hardware or virtualized, capable of calculating at least one temperature difference between at least two temperatures.
3. may store values or tables for at least one temperature cutoff threshold and at least one temperature difference threshold.
4. automatically compare at least one temperature to a temperature cutoff threshold, one temperature difference to a difference cutoff threshold, and report results from the comparisons.
5. contain at least one method of communication and/or display capable of being used to identify and/or notifying an operator of comparison results.

Ideally, systems may be capable of making on-the fly changes to threshold cutoff values or tables based on environmental or other adaptations, may be capable of selfcalibration and able to store historical data and results for recall, though this is not a requirement.

Optionally, systems may be capable of displaying and communicating pass/fail criterion to operators in real time.

The teachings of this disclosure can be employed within any type of work, public, educational, sports, military, recreational, or health space. A few nonlimiting examples include high rise office buildings or complexes, retail malls, government buildings, schools, higher education facilities, aircraft, cinemas, sports events, military bases, ships, hospitals, nursing homes, doctors' offices, fitness complexes, health centers, hotels and the like.

In one embodiment, Region 2 is measured using a temperature enabled smart watch that records wrist temperature, and Region 1, face temperature, is recorded by a smart IR sensor embedded on a mobile device. Both temperatures may be uploaded to a cloud-based app, where differences and cutoff thresholds are applied, and the device owner is notified through the app if evaluated as febrile. In another embodiment, both region temperatures are measured and recorded with a smart mobile device, Region 1 temperature is measured using a built-in IR thermal imager and fingertip temperatures are measured for Region 2, through transducing sensors embedded in the device case. In this embodiment the evaluation app is stored locally on the mobile device. In yet another embodiment, a thermal imager is integrated to a vehicle dashboard and measures occupants face and hand temperatures. Pre-installed software may be loaded into the vehicle's processor and evaluates temperatures and difference cutoffs and notifies drivers and passengers of febrile identifications.

Therefore, in one embodiment, the disclosure teaches a system configured to characterize subject body temperatures as normal or febrile, wherein the system comprises: (a) a measurement device for capturing and displaying at least one body temperature of a subject, wherein the transducer is configured to measure a temperature that positively correlates with deep body temperature (Region 1); (b) a method for assessing and characterizing the temperature from this transducer as elevated, wherein, a protocol is used to correlate body temperature measured by the transducer to deep body temperature, and this temperature is characterized as normal or elevated and is not necessary to refer to traditional definitions of febrile temperatures; (c) a second transducer, configured to measure and display at least one temperature from a peripheral body region that may undergo deep tissue vasoconstriction (Region 2); (d) a method employed to compare differences between Region 1 and Region 2 temperatures; (e) if Region 1 temperature is characterized as elevated, then the difference between Region 1 and Region 2 temperatures are used to confirm a febrile result, wherein this is compared to a predefined difference cutoff threshold; (f) febrile characterization is rendered, wherein a febrile characterization is determined only when Region 1 temperature is identified as elevated, and a difference between two regional temperatures exceeds a predetermined threshold; (g) after a febrile characterization has been rendered, this apparatus has the capability to display and/or provide at least one notification to enable action on the result. In one embodiment the temperature of Region 1 and/or Region 2 are measured using an infrared thermometer or thermal imager. In another embodiment temperatures of Region 1 and Region 2 are made simultaneously. In one embodiment temperatures of Region 1 and Region 2 are made using a single transducer. In another embodiment Region 1 and/or Region 2 temperatures are averaged over areas of >2 mm$^2$. In one embodiment the absolute temperature of Region 2 is used as a second temperature cutoff, instead of the temperature difference. In another embodiment a cutoff threshold for Region 1 temperature is adjusted based upon situational and environmental conditions. In one embodiment a cutoff threshold for Region 1 temperature is adjusted based upon the difference between Region 1 and Region 2 temperatures. In another embodiment a cutoff threshold for Region 1 temperature is regularly updated based upon the most recent test screening data. In one embodiment a cutoff threshold for differences between Region 1 and Region 2 temperatures is adjusted based upon situational and environmental conditions. In another embodiment a cutoff threshold for differences between Region 1 and Region 2 temperatures is adjusted based upon Region 1 temperature. In one embodiment a cutoff threshold for differences between Region 1 and Region 2 temperatures is regularly updated based upon the most recent data. In another embodiment wherein the cutoff threshold for Region 1 is made using an average of more than one region. In one embodiment the cutoff threshold for differences is made between more than two regional temperatures. In another embodiment a probability of infection is predicted based on Region 1 and Region 2 Temperature measurements. In one embodiment a processor is configured to continually make febrile predictions using realtime or near real-time temperature measurement data.

In one aspect, the disclosure provides a method of detecting a disease, comprising using the system of the disclosure. In one embodiment, the disease is caused by an infection. In another embodiment, the disease is coronavirus Disease 2019 (COVID-19).

In one aspect, the disclosure provides a method of predicting infection epidemiology, comprising using the system of the disclosure.

What is claimed is:

1. A system to perform fever screening of a subject body to determine a true febrile state, comprising:
    at least one measurement device to simultaneously capture a first temperature from a first region of the body that correlates with deep body temperature and a second temperature from a second peripheral body region that undergoes deep tissue vasoconstriction; and
    a processor programmed to:
        compute a difference between the first temperature and the second temperature;
        determine whether the first temperature exceeds a first threshold;
        when the first temperature exceeds the first threshold characterize the subject as febrile when the difference between the first temperature and the second temperature exceeds a second threshold; and
        issue an alert when the subject is characterized as febrile.

2. The system of claim 1, wherein the at least one measurement device is an infrared thermometer or thermal imager.

3. The system of claim 2, wherein temperature measurements of the first region and the second peripheral region are made simultaneously.

4. The system of claim 1, wherein temperature measurements of the first region and the second peripheral region are made using a same measurement device.

5. The system of claim 1, wherein the first region temperatures, or the second region temperatures, or both the first region and the second peripheral region temperatures are averaged over surface areas of >2 mm2.

6. The system of claim 1, wherein the temperature of the second region is used as a second temperature cutoff.

7. The system of claim 1, wherein the first threshold for the first region temperature is adjusted based upon situational conditions, or environmental conditions, or both situational conditions and environmental conditions.

8. The system of claim 1, wherein the first threshold for the first region temperature is adjusted based upon the difference between the first region and the second peripheral region temperatures.

9. The system of claim 1, wherein the first threshold for the first region temperature is regularly updated based upon recent test screening data.

10. The system of claim 1, wherein the second threshold is adjusted based upon situational conditions, or environmental conditions, or both situational conditions and environmental conditions.

11. The system of claim 1, wherein the second threshold is adjusted based upon the Region 1 temperature.

12. The system of claim 1, wherein the second threshold is regularly updated based upon recent data.

13. The system of claim 1, wherein the first threshold comprises an average of more than one area on the subject.

14. The system of claim 1, wherein:
the at least one measurement device is further configured to capture a third temperature measurement from another body region; and
the processor is further programmed to characterize the subject as febrile based on a combination of the difference between the first temperature and the second temperature and a difference between the first temperature and the third temperature.

15. The system of claim 1, wherein a probability of infection is predicted based on the first region and the second peripheral region temperature measurements.

16. The system of claim 1, wherein the processor is further configured to continually make febrile predictions using real-time or near real-time temperature measurement data.

17. A method of performing fever screening of a subject body to determine a true febrile state, the method comprising:
simultaneously capturing a first temperature in a first region that correlates with deep body temperature and a second temperature in a second region from a peripheral body region that undergoes deep tissue vasoconstriction;
computing, with a specifically programmed computer processor, a difference between the first temperature and the second temperature;
determining, with the specifically programmed computer processor, that a true febrile state exists when the first temperature is above a first threshold and the difference between the first temperature and the second temperature exceeds a second threshold; and
issuing an alert when the determination is made that a true febrile state exists.

18. The method according to claim 17, wherein the determining that a true febrile state exists also includes determining that a disease exists.

19. The method according to claim 18, wherein the disease is caused by an infection.

20. The method according to claim 18, wherein the disease is a coronavirus disease.

21. The method according to claim 18, wherein the coronavirus disease is COVID-19.

* * * * *